United States Patent
Vestal

(10) Patent No.: US 11,232,940 B2
(45) Date of Patent: *Jan. 25, 2022

(54) METHOD AND APPARATUS FOR SURGICAL MONITORING USING MALDI-TOF MASS SPECTROMETRY

(71) Applicant: Virgin Instruments Corporation, Marlborough, MA (US)

(72) Inventor: Marvin L. Vestal, Framingham, MA (US)

(73) Assignee: Virgin Instruments Corporation, Marlborough, MA (US)

( * ) Notice: Subject to any disclaimer, the term of this patent is extended or adjusted under 35 U.S.C. 154(b) by 789 days.

This patent is subject to a terminal disclaimer.

(21) Appl. No.: 15/662,581

(22) Filed: Jul. 28, 2017

(65) Prior Publication Data

US 2018/0040467 A1 Feb. 8, 2018

Related U.S. Application Data

(60) Provisional application No. 62/370,109, filed on Aug. 2, 2016.

(51) Int. Cl.
*A61B 5/00* (2006.01)
*H01J 49/16* (2006.01)
(Continued)

(52) U.S. Cl.
CPC .......... *H01J 49/164* (2013.01); *A61B 5/0036* (2018.08); *A61B 5/0075* (2013.01);
(Continued)

(58) Field of Classification Search
CPC .. C12Q 2543/10; C12Q 1/6886; A61B 10/00; A61B 10/02; A61B 34/30; A61B 5/0075;
(Continued)

(56) References Cited

U.S. PATENT DOCUMENTS 4,314,156 A * 2/1982 Kuppermann ........ H01J 49/022
250/281
5,742,050 A * 4/1998 Amirav ............... H01J 49/0422
250/287
(Continued)

OTHER PUBLICATIONS

Calligaris, et al., Mass Spectrometry Imaging as a Tool for Surgical Decision-Making; J. Mass Spectrom Nov. 2013, 2 Pages, vol. 48, No. 11.

*Primary Examiner* — May A Abouelela
(74) *Attorney, Agent, or Firm* — Rauschenbach Patent Law Group, LLC; Kurt Rauschenbach

(57) ABSTRACT

An apparatus for monitoring a surgical procedure includes a MALDI-TOF mass spectrometer comprising a load lock, an ionization chamber, and an ion detector. A first video camera produces an optical image of an operating field of the surgical procedure. A sample extracting device extracts the tissue sample at the location within the optical image of the operating field. A sample preparation system prepares MALID-TOF samples by depositing an extract of the extracted tissue sample on a sample plate together with a MALDI matrix. A sample plate loading mechanism loads the sample plate into the MALDI-TOF mass spectrometer. A second video camera produces an optical image of the sample plate and records a location of the extracted tissue sample. A computer records the images from first and second video cameras, correlates the location of the tissue sample in the operating field with the location of the tissue sample on the sample plate, acquires mass spectra data from the MALDI-TOF mass spectrometer, and compares the mass spectrum data to known mass spectrum data.

14 Claims, 3 Drawing Sheets

(51) Int. Cl.
  *H01J 49/00* (2006.01)
  *H01J 49/04* (2006.01)
  *H01J 49/40* (2006.01)
  *A61B 90/00* (2016.01)
  *A61B 10/02* (2006.01)

(52) U.S. Cl.
  CPC .......... *A61B 10/0233* (2013.01); *A61B 90/36* (2016.02); *H01J 49/0031* (2013.01); *H01J 49/0081* (2013.01); *H01J 49/0413* (2013.01); *H01J 49/40* (2013.01); *A61B 5/0077* (2013.01); *A61B 2090/371* (2016.02); *A61B 2505/05* (2013.01)

(58) Field of Classification Search
  CPC ... A61B 90/36; A61B 10/0233; A61B 5/0077; H01J 49/0036; H01J 49/0072; H01J 49/165; H01J 49/164; H01J 49/0081; H01J 49/0413; H01J 49/40; H01J 49/0031
  USPC ........ 600/562, 564; 250/281, 282, 285–288; 435/7.1
  See application file for complete search history.

(56) References Cited

U.S. PATENT DOCUMENTS

| | | | | |
|---|---|---|---|---|
| 5,841,136 | A * | 11/1998 | Hoile | H01J 49/0418 250/288 |
| 7,064,319 | B2 * | 6/2006 | Hashimoto | H01J 49/004 250/287 |
| 7,180,058 | B1 * | 2/2007 | Izgarian | H01J 27/24 250/281 |
| 7,435,951 | B2 * | 10/2008 | Truche | G03B 15/07 250/281 |
| 7,495,231 | B2 * | 2/2009 | Truche | G03B 15/07 204/462 |
| 7,564,026 | B2 * | 7/2009 | Vestal | H01J 49/025 250/287 |
| 7,564,028 | B2 * | 7/2009 | Vestal | B08B 1/00 250/281 |
| 7,663,100 | B2 * | 2/2010 | Vestal | H01J 49/406 250/287 |
| 7,851,744 | B2 * | 12/2010 | Brown | G02B 27/0977 250/284 |
| 8,058,610 | B2 * | 11/2011 | Harada | H01J 49/164 250/288 |
| 8,735,810 | B1 | 5/2014 | Vestal | |
| 9,214,323 | B1 | 12/2015 | Vestal et al. | |
| 9,362,095 | B1 * | 6/2016 | Hayden | H01J 49/0409 |
| 9,443,707 | B2 | 9/2016 | Hayden et al. | |
| 9,536,716 | B2 * | 1/2017 | Ikegami | H01J 49/004 |
| 2003/0180807 | A1 * | 9/2003 | Hess | B01L 3/5025 435/7.1 |
| 2005/0279933 | A1 * | 12/2005 | Appelhans | H01J 49/10 250/296 |
| 2006/0087651 | A1 * | 4/2006 | Montaser | G01N 15/065 250/288 |
| 2009/0146053 | A1 * | 6/2009 | Setou | H01J 49/164 250/281 |
| 2011/0244479 | A1 * | 10/2011 | Schultz | B82Y 30/00 435/7.1 |
| 2013/0168545 | A1 * | 7/2013 | Clem | H01J 49/0463 250/282 |
| 2013/0187041 | A1 * | 7/2013 | Brouard | H01J 49/403 250/282 |
| 2013/0308756 | A1 * | 11/2013 | Bogan | H01J 49/04 378/86 |
| 2013/0344111 | A1 * | 12/2013 | Roder | A61K 39/0011 424/274.1 |
| 2014/0072476 | A1 * | 3/2014 | Otsuka | H01J 49/0454 422/83 |
| 2014/0296089 | A1 * | 10/2014 | Holmes | G01N 15/1475 506/9 |
| 2015/0287578 | A1 * | 10/2015 | Bendall | H01J 49/0036 250/282 |
| 2015/0332906 | A1 * | 11/2015 | Bark | H01J 49/0036 250/282 |
| 2016/0099139 | A1 * | 4/2016 | Kyogaku | H01J 49/004 250/287 |
| 2016/0341712 | A1 * | 11/2016 | Agar | G01N 33/57496 |
| 2018/0047551 | A1 * | 2/2018 | Jones | H01J 49/0459 |
| 2018/0047555 | A1 * | 2/2018 | Pringle | A61B 18/1815 |
| 2018/0103935 | A1 * | 4/2018 | Pringle | G01N 33/487 |
| 2018/0197726 | A1 * | 7/2018 | Yamaguchi | G06K 9/4652 |

* cited by examiner

METHOD AND APPARATUS FOR SURGICAL MONITORING USING MALDI-TOF MASS SPECTROMETRY

The section headings used herein are for organizational purposes only and should not to be construed as limiting the subject matter described in the present application in any way.

RELATED APPLICATION SECTION

The present application is a non-provisional application of U.S. Provisional Application Ser. No. 62/370,109, filed on Aug. 2, 2016, entitled "Method and Apparatus for Surgical Monitoring Using MALDI-TOF Mass Spectrometry". The entire contents of U.S. Provisional Patent Application Ser. No. 62/370,109 are herein incorporated by reference.

INTRODUCTION

It is widely recognized in the art that automated prediction, diagnosis, and management of diseases is a realistic goal using mass spectrometers suitable for clinical applications. Early diagnosis has obvious benefits in that it allows physicians to begin treatments sooner. Properly identifying disease sub-classification also allows physicians to tailor treatments to specific patients, thereby greatly improving treatment outcomes. Mass spectrometric imaging (MSI) methods are now available for medical diagnostic applications. One important application is clinical histopathology. Mass spectrometric imaging methods can provide excellent histological specificity, often going well beyond just the identification of morphological tissue types, but these techniques have not yet made the transition into to daily clinical routine.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way.

DESCRIPTION OF VARIOUS EMBODIMENTS

Figure 1:
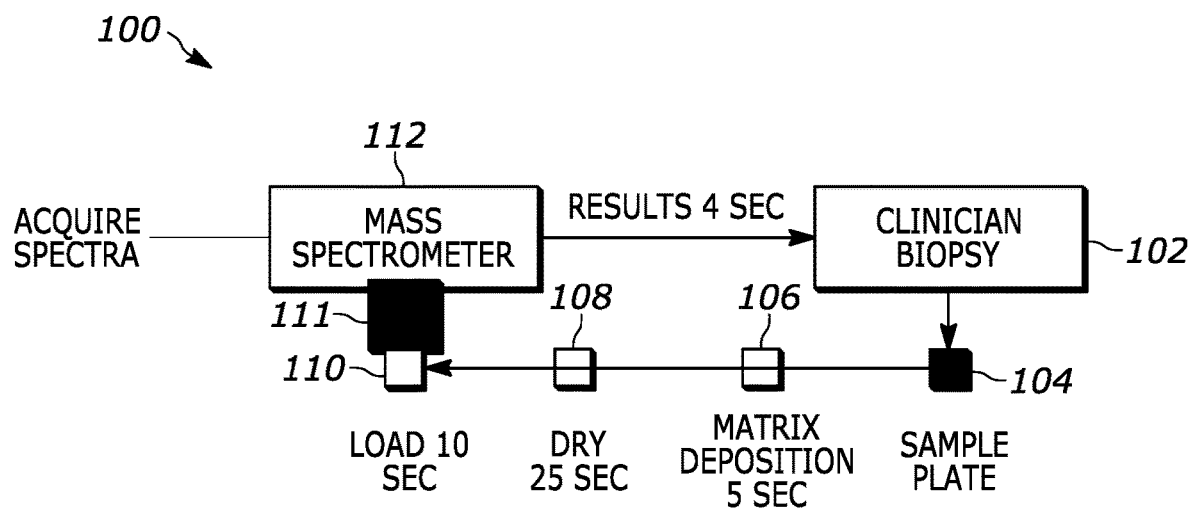
FIG. 1 illustrates a block diagram of an automated surgical monitoring method and apparatus for in vivo analyses using MALDI-TOF mass spectrometer according to the present teaching.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings can be performed in any order and/or simultaneously as long as the teaching remains operable. Furthermore, it should be understood that the apparatus and methods of the present teaching can include any number or all of the described embodiments as long as the teaching remains operable.

Surgical intervention is a primary treatment option for many tumors. The best patient outcomes are dependent on absolute tumor resection, ideally minimizing damage to adjacent normal tissue, and reducing surgery time. Several approaches for monitoring surgical procedures have been proposed and evaluated. Direct examination of biological tissue by mass spectrometry (MS) began in the 1970s, but the methods available at that time did not provide useful information on the chemical composition of the samples tested.

The first breakthrough came with desorption ionization methods such as secondary ionization mass spectrometry (SIMS) and matrix-assisted laser desorption ionization (MALDI). Recently, rapid evaporative ionization mass spectrometry (REIMS), which was first described in 1999, has been used as well as direct electrospray (DESI) method. Chemical biological tissue imaging analysis can be achieved using these methods, after appropriate sample preparation. From the late 1990s, it became apparent that mass spectrometry data in imaging studies showed a high degree of tissue specificity, and that tissue histology could determine mass spectral information, and vice versa. As such, mass spectrometry is a potentially powerful tool to aid surgical intervention for tumors. However, prior art mass spectrometry methods and apparatus lacked the form factor, speed, resolution, specificity, signal-to-noise-ratio, and automation required to make a system appropriate for integration into the operating room and/or surgical procedure.

A potential advantage of mass spectrometric imaging for the evaluation of tumor margins is the ability to identify molecular changes that are not detectable by histopathological evaluation alone. Matrix Assisted Laser Desorption/Ionization Time-of-Flight Mass Spectrometry (MALDI-TOF MS), Rapid Evaporative Ionization Mass Spectrometry (REIMS), and Desorption Electrospray (DESI) have been used successfully for mass spectrometric imaging applications. Advantages of MALDI-TOF over DESI or REIMS include the fact that the mass spectrometer module is not directly connected to the patient or surgeon, and also that it is located outside the immediate sterile environment. Furthermore, protein profiles, lipid profiles, and metabolic profiles can all be obtained on each sample if necessary.

Recent improvements in Matrix-Assisted Laser Desorption/Ionization Time-of-Flight Mass Spectrometry provide particularly powerful tools for clinical assays of bodily fluids and tissues. See, for example, U.S. Pat. No. 8,735,810, entitled "Time-of-Flight Mass Spectrometer with Ion Source and Ion Detector Electrically Connected", U.S. Pat. No. 9,214,323, entitled "Method and Apparatus for Transporting Sample Plates Between Chambers of a Mass Spectrometer" and U.S. Pat. No. 9,362,095, entitled "Method and Apparatus for Transporting Samples in a Mass Spectrometer", and U.S. patent application Ser. No. 15/044,934, filed on Feb. 16, 2016, entitled "Method and Apparatus for Transporting Samples in a Mass Spectrometer". U.S. Pat. Nos. 8,735,810, 9,214,323, and 9,362,095 and U.S. patent application Ser. No. 15/044,934 are assigned to the present assignee and are incorporated herein by reference.

The MALDI-TOF systems of the present teaching include a load lock that receives a sample plate supporting samples for analysis, an ionization chamber that ionizes the samples, and an ion detector that detects the ionized samples. The MALDI-TOF techniques provide a combination of high-sensitivity, wide-dynamic range, and high-throughput. Additionally, these techniques are effective with transferring and analysis of only a very small volume of a sample (ca. 1 nanoliter). Consequently, these techniques are rapidly becoming practical for routine clinical testing. MALDI-TOF MS is advantageous because it provides both qualitative and quantitative information about the sample. Instruments designed for routine clinical applications are fully automated, requiring little or no operator expertise in mass spectrometry.

Earlier mass spectrometric imaging (MSI) techniques are generally considered to be too slow to be widely used, with analysis times for a single clinical section ranging from hours to days. In contrast, the MALDI-TOF system of the present teaching currently provides images at speeds of approximately 100 pixel/sec and at pixel sizes as small as 20 µm. This performance will certainly improve over the next few years. Although this resolution may not allow the proper identification of single cells, this resolution does correspond well to small groups of cells in a histological matrix. The overall diagnostic strategy allows the analysis of individual sections in the timeframe of less than one minute, approaching the expectations of histopathology services.

Furthermore, a new sample loading mechanism has been developed and implemented that allows sample plates to be loaded from atmosphere to the vacuum of the mass spectrometer in less than 10 sec. This sample loading mechanism make the mass spectrometer analysis very fast compared to the time required for the surgery and acquisition of samples. With these systems, the time required to prepare multiple samples and load them into the MALDI-TOF is less than 1 minute, and parallel digestion of multiple samples can also be done on a similar time scale using immobilized enzymes. If it takes 10 minutes to do the surgery and to take samples, the mass spectrometer of the present teaching can analyze at least 100 separate samples in that time. Furthermore, high-resolution (25 µm) imaging can be carried out at rate of 4 mm²/min.

A wide variety of sampling devices and methods can be employed for acquiring samples during surgery. One suitable sampling device is a fine needle biopsy device for sampling neural tissue during tumor resection. Mass spectrometer data acquisition and interpretation for multiple samples requires less than one minute and can provide metabolite, lipid, and protein mass spectrometer profiles that can be validated by traditional histopathology to differentiate diseased and normal tissue.

MALDI-TOF mass spectrometry provides multiple options for the direct characterization of tissue to support surgical decision-making, and provides significant insight into the development of drugs targeting tumors of the central nervous system (CNS). Operating conditions and MALDI matrices may be chosen to rapidly analyze specific tumor markers such as metabolites, fatty acids, lipids, and proteins from surgical tissue for surgical guidance and rapid diagnosis. Similar clinical protocols may be employed to visualize drug and metabolites penetration in brain tumor tissue, and to correlate with tumor heterogeneity and response to support drug development.

Surgical intervention is the primary treatment option for brain tumors. The best patient outcomes occur when absolute tumor resection is accomplished with minimum damage to adjacent normal tissue and the minimum surgery time. The MALDI-TOF mass spectrometer of the present teaching provides molecular-based diagnostics on a timescale compatible with the surgery time. A combination of using a fine needle biopsy device for sampling neural tissue during tumor resection, rapid mass spectrometry data acquisition, and interpretation for multiple samples in less than one minute can provide metabolite, lipid, and protein mass spectrometry profiles that can be validated by traditional histopathology to differentiate diseased and normal tissue.

The method of the present teaching utilizes MALDI-TOF mass spectrometers that generate accurate quantitative data by providing reproducible spectra on complex samples. In these instruments, the laser repetition rate is in the 1- to 10-kHz range, and the laser spot is rastered over the sample. These instruments are designed for routine clinical applications and are fully automated and require little or no expertise in mass spectroscopy. The user prepares the samples according to a protocol established for the particular application, loads the sample plates into the instrument, and receives and interprets the results. The instrument parameters are determined from data provided with the samples, data acquisition, processing, and database searching. The instrument can be fully automated. No other interaction between the user and the instrument is required.

The surgical monitoring MALDI-TOF mass spectrometry apparatus of the present teaching provides the flexibility needed to accommodate a variety of important applications. Some methods according to the present teaching target high-resolution tissue imaging. Spectra can be produced by averaging 100 laser shots per pixel and generated at rates of 100 pixels/s with pixel sizes less than 20 µm. Rastering a laser beam over a sample spot a plurality of times ionizes a large fraction of the clinical sample on a sample spot. In some embodiments, a large fraction of the sample is ionized and analyzed on a sample spot. At least 10,000 laser shots are typically summed to obtain a spectrum. As many as 500,000 laser shots can be used, if necessary, to completely ionize a sample.

Analyzing a large fraction of ionized samples provides reproducible mass spectra with no significant noise. Such conditions are consistent with using multiple instruments and having multiple users preparing samples. Analyzing a large fraction of ionized samples also minimizes effects due to variations in the amount and distribution of samples on the sample plate. The surgical monitoring MALDI-TOF mass spectrometry apparatus of the present teaching effectively reduces the variability of the results due to instrument imperfections to the point that this effect is negligible in the quality of the results obtained. The remaining sources of uncontrolled variability are sample preparation and deposition on the sample plate. These effects are the dominant reasons for variability in resolving power and measured masses and intensities of the peaks in the spectrum.

One feature of the present teaching is the ability to implement MALDI-TOF mass spectrometry in time periods that are short enough to enable in vivo applications. The surgical monitoring MALDI-TOF mass spectrometry apparatus of the present teaching uses a sample loading mechanism that allows sample plates to be loaded from atmosphere to the vacuum of the mass spectrometer in less than 10 sec.

FIG. 1 illustrates a block diagram of an automated surgical monitoring method and apparatus 100 for in vivo analyses using a MALDI-TOF mass spectrometer according to the present teaching. The method and apparatus 100 starts with the clinician 102 taking a biopsy during surgery. Numerous types of clinical biological sampling methods can be used by the clinician 102 to perform the biopsy during surgery. A sampling module can be located in the surgery environment. The MALDI-TOF mass spectrometer is typically located in close proximity, but not necessarily in, the operating room.

One feature of the method and apparatus 100 of automated surgical monitoring for in vivo analyses using MALDI-TOF mass spectrometer according to the present teaching is that it provides effective diagnostic outcomes using only a small volume of biological material. A number of sampling devices are now available for obtaining small volumes of biological samples in vivo. One sampling device is the CE-IVD Mitra™ Microsampler from neoteryx. This sampling device is designed to accurately sample 10 µL of bodily fluid including blood, urine, or saliva. Another sampling device uses the well-known technique of fine-needle aspiration. Fine-needle aspiration biopsy devices and fine-needle aspiration cytology devices are sampling devices for diagnostic procedures used to investigate superficial lumps or masses. In these techniques, the sampling device may be a thin, hollow needle is inserted into the mass for sampling of cells that, after being stained, will be examined under a microscope. Using these techniques, almost any volume greater than ca. 1 nanoliter of either bodily fluid or solid tissue can be sampled.

The biopsied tissue is then prepared for mass spectrometry analysis. First, the biopsied tissue is deposited on a sample plate 104. A matrix material is then deposited on the biopsied tissue in a deposition apparatus 106. The matrix material is then dried in an oven 108 or other drying area. The tissue biopsy is then loaded into a loadlock 110 of a MALDI TOF mass spectrometer 112 where it can then be loaded into the mass spectrometer 112 by a sample plate loading mechanism 111. In some embodiments, the matrix deposition 106 step of the method is completed in about five seconds. The step of drying in the oven 108 is completed in about twenty-five seconds, and the step of loading into a loadlock 110 is completed in about ten seconds.

The residual tissue biopsy prepared for mass spectrometry and loaded into the loadlock 110 of the MALDI TOF mass spectrometer 112 is then evaluated using the MALDI-TOF mass spectrometer 112 of the present teaching. For example, the mass spectrometer 112 can be a standard commercial mass spectrometer instrument, such as the SimulTOF ONE, which is manufactured by the present assignee. One skilled in the art will appreciate that even simpler instruments customized for in vivo applications may be used. In working embodiments of the MALDI TOF mass spectrometer 112, the time between presenting a sample plate to the automated system and acquisition of spectra is approximately 40 seconds. For a nominal total analysis time of one minute, and allowing 4 seconds for interpretation and transmission of results, spectra from 160,000 laser shots are available. Such a mass spectrometer may be used to image 1 mm$^2$ of tissue at 100 shots/pixel and 25 µm spatial resolution. For very high dynamic range, 10,000 shots can be performed on each of 16 samples, or all 160,000 on a single sample.

The MALDI-TOF-MS evaluation results are classified and compared with standard histopathology. The method and apparatus 100 of automated surgical monitoring using MALDI-TOF mass spectrometer for in vivo analyses according to the present teaching can be repeated any number of times as necessary. Improvements to the tissue analysis process using the method of the present teaching in the operating room will increase analysis speed and significantly decrease the time required for pathological evaluation of neural tissue.

Figure 1B:
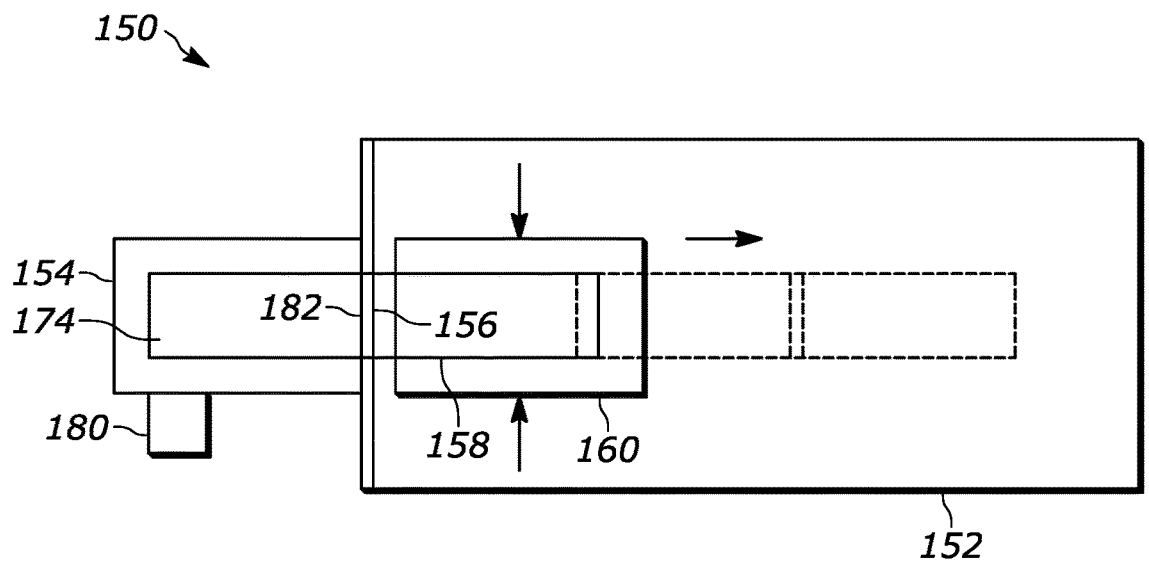
FIG. 1B illustrates a diagram for one embodiment of a sample plate handling system for a mass spectrometer, according to the present teaching.

FIG. 1B illustrates a diagram for one embodiment of a sample plate handling system for a mass spectrometer, according to the present teaching. The sample plate handling system 150 comprises a mass spectrometer chamber 152 and a transport chamber 154 connected by sealing orifice 156. A portion of the sample plate transporter 158 or loading mechanism is mounted on a two-dimensional translation stage 160. For example, the two-dimensional translation stage can be an X-Y translation stage. Motion in the x-direction aligns the sample plate transporter 158 with orifice 156, and motion in the y-direction moves the sample plate transporter 158 so that sample plate 174, which is mounted on sample plate transporter 158, is moved through sealing orifice 156 into and out of the mass spectrometer chamber 152.

The sample plate handling system 150 further comprises an interface 182 having a means for sealing orifice 156 when the sample plate transporter 158 is extended, so that sample plate 174 is fully within transport chamber 154. A vent valve 180 is opened to allow air to flow into transport chamber 154 when orifice 156 is sealed in order to bring the pressure in transport chamber 154 to atmospheric pressure while maintaining high vacuum in mass spectrometer chamber 152.

Figure 2A:
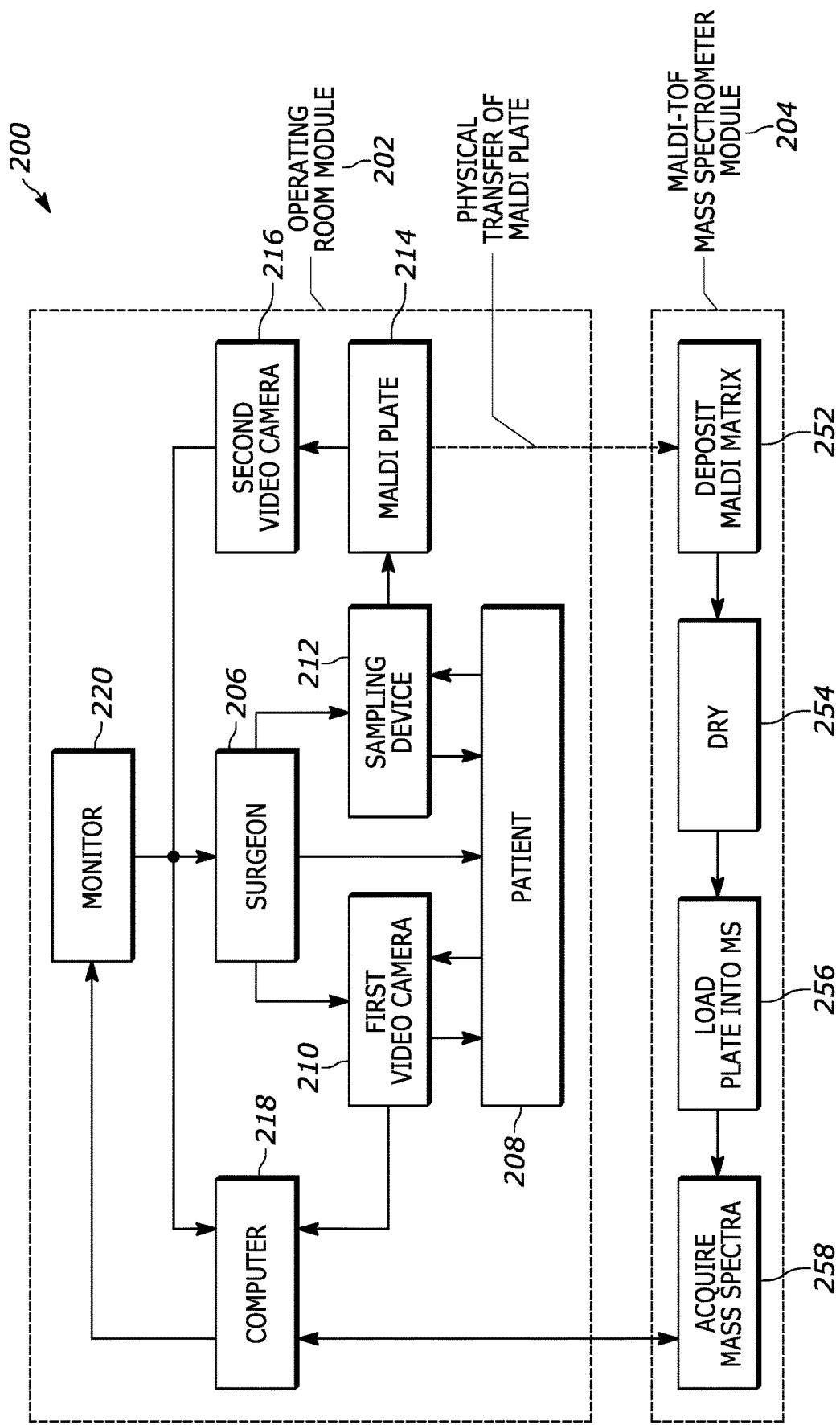
FIG. 2A illustrates a block diagram of an integrated system and method for surgical monitoring according to the present teaching.

FIG. 2A illustrates a block diagram of an integrated system and method 200 for surgical monitoring according to the present teaching. The integrated system and method 200 includes an operating room module 202 that is positioned in the surgical environment and a MALDI-TOF mass spectrometer processing module 204. The operating room module 202 is integrated into the surgical procedure being performed on the patient 208 by the surgeon 206. The MALDI-TOF mass spectrometer processing module 204 is typically located in close proximity. In some embodiments, the MALDI-TOF mass spectrometer is in the operating room. In other embodiments, the MALDI-TOF mass spectrometer is outside of the operating room. However, one skilled in the art will appreciate that the MALDI-TOF mass spectrometer processing module 204 only needs to be in a location where it can be rapidly accessed to receive the tissue biopsy and to perform the required MALDI mass spectrometer measurements in the required time period. One feature of the methods and apparatus of the present teaching is that the mass spectrometer processing module 204 is not directly connected to the patient or surgeon, and is located outside the immediate sterile environment. This feature reduces the cost of the operating environment and also allows for either larger and/or less expensive mass spectrometry equipment.

More specifically, the operating room module 202 comprises a first video camera 210 for viewing and recording the operating field on the patient 208 at high spatial resolution, and a sampling device 212 that is controlled by the surgeon 206 for taking a small sample of tissue or fluid from the patient 208 and transferring the sample to a MALDI sample plate 214. The MALDI plate sample preparation 214 may be a robotic mechanism. The sample plate may be labeled using a bar code. The first video camera 210 records the location of the sample within the operating field on the patient, and a second video camera 216 records the corresponding location of that sample on the MALDI plate 214.

Both the first and second video cameras 210, 216 are interfaced to a computer 218 that correlates the sampled position on the patient 208 with the position of that sample on the MALDI plate 214. Any type of interface between the computer and the first and second video cameras 210, 216 can be used. For example, the interface can be a hardwired interface or can be a wireless interface. The positions of the sampled location within the operating field are displayed on the monitor 220 that is viewed by the surgeon 206. When the surgeon 206 determines that enough positions have been sampled, he initiates transfer of the MALDI plate 214 to the MALDI-TOF mass spectrometer processing module 204.

In some methods, the computer 218 provides information about the clinical samples to the MALDI-TOF mass spectrometer processing module 204. The MALDI-TOF mass spectrometer processing module 204 produces mass spectra from the sample, and returns the results to the computer 218 where they can be displayed on a monitor 220. The computer prepares the results for the surgeon 206 to view on the monitor 220. In some methods, the computer changes parameters in the MALDI-TOF mass spectrometer processing module 204 based on the generated mass spectrum.

Figure 2B:
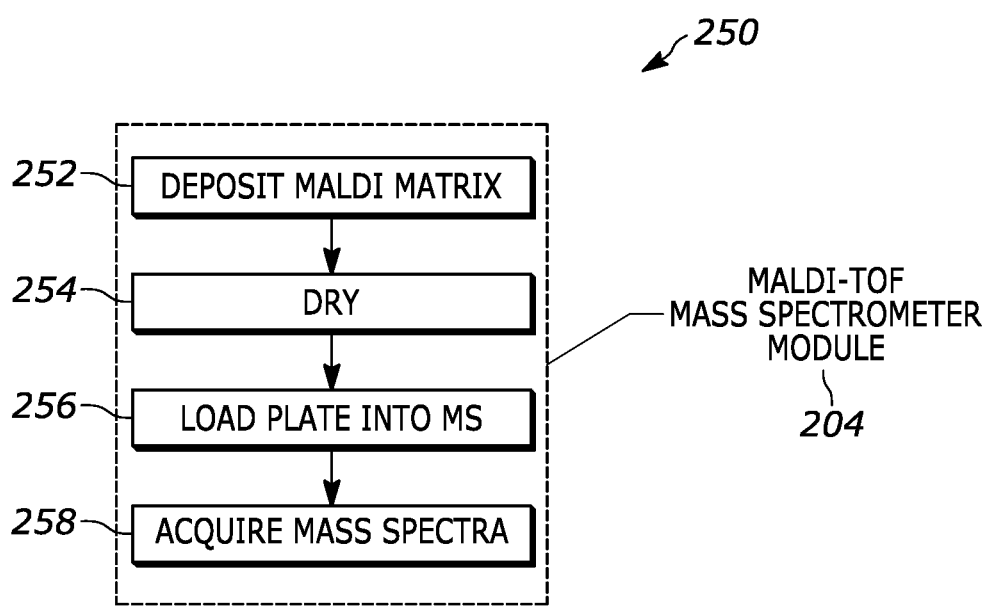
FIG. 2B illustrates a method performed by the MALDI-TOF mass spectrometer processing module for MALDI-TOF mass spectrometry on the biopsy tissue according to the present teaching.

FIG. 2B illustrates a method 250 performed by the MALDI-TOF mass spectrometer processing module 204 for MALDI-TOF mass spectrometry on the biopsy tissue. In the first step 252 of the method 200, the mass spectrometer processing module 204 deposits MALDI matrix material into the samples. In the second step 254 of the method 200, the samples with MALDI matrix applied are dried 254. In the third step 256 of the method 200, the dried samples on the sample plate are loaded into the MALDI-TOF mass spectrometer 256 load lock and then into an evacuated ion source chamber of the mass spectrometer for ionization. The sample plate loading in the third step 256 may be automated, using an autoloader, or may be manual loaded. In various methods according to the present teaching, the sample plate loading mechanism may be configured with a microtiter format or an array format.

In the fourth step 258 of the method 200, a mass spectra is acquired for each sample on the MALDI plate 214 with the MALDI-TOF mass spectrometer 256. The MALDI-TOF mass spectrometer 256 ionizes the prepared samples on the plate samples with either positive or negative ions. Ions are detected using an ion detector. In some configurations, the sample plate and ion detector is biased at ground potential.

Numerous types of MALDI-TOF mass spectrometers can be used with the methods and apparatus of the present teaching. In various embodiments of the apparatus and methods of the present teaching, the MALDI-TOF mass spectrometer is a linear TOF analyzer. However, in some applications, higher resolution is required. In these applications, a tandem MALDI-TOF mass spectrometer and/or a reflector MALDI-TOF mass spectrometer can be used.

In some embodiments, the MALDI TOF mass spectrometer can include a bar code reader and a processor that receives instructions and other data from a computer. In these embodiments, referring back to FIG. 2A, the MALDI-TOF mass spectrometer processing module 204 correlates the sample plate being analyzed with associated processing instructions from the computer 218. In other embodiments, the computer 218 passively acquires data from the MALDI TOF mass spectrometer without receiving any instructions MALDI TOF mass spectrometer.

The total time to accomplish the process for MALDI-TOF mass spectrometry integrated with an operating room module including the time to prepare the clinical samples for MALDI-TOF mass spectrometry by depositing an extract of the clinical samples on a sample plate together with a MALDI matrix 252, drying the samples 254, loading the plates 256 into a mass spectrum chamber, and then ionizing the clinical samples on the sample plate, acquiring a mass spectra 258, and sending the mass spectra to a computer 218 for processing and analysis is typically less than 40 seconds. The acquisition time for acquiring the mass spectra 258 depends on the number of samples and the number of laser shots summed. In many practical methods, the acquisition time is less than 15 seconds.

After the mass spectrum is acquired, it is transferred to the computer 218. The computer 218 may perform peak detection on the mass spectrum using a wavelet method to determine if a predetermined intensity is exceeded. The mass spectrum is interpreted using various known methods. The computer 218 correlates the spectra with the sampled position. In some embodiments, the spectra obtained by the surgical monitoring with the MALDI-TOF Mass Spectrometry method and apparatus of the present teaching may be interpreted by comparing the results with spectra that have been obtained offline for cancerous and normal tissue. The comparison between the acquired results and the offline-obtained results are shown on the monitor 220 viewed by the surgeon 206. The viewing by the surgeon 206 is typically done in real-time during surgery.

One feature of the method of the present teaching is that it can be used to identify cells that are cancerous, cells that are normal, cells that are mixed, and cells that are indeterminate. The methods can also be used to determine if the cells are indicative of a particular type of tumor. Based on the identification made by the computer, the individual spots from the processed sample may be displayed on the monitor 220 in various colors to indicate the type of cells. For example, individual spots can be displayed as red for cancer, green for normal, or yellow for mixed or indeterminate in order to give the surgeon rapid feedback to make decisions and continue the surgical procedure.

Another feature of the methods of the present teaching is that they can be used to highlight tissue-specific expression of detected proteins. The methods of the present teaching can be used to detect protein and peptide components with the tissue-specific expression of proteins that are commonly known. Precise immunohistochemical methods are based on this phenomenon. Tissue-specific results can also be obtained from cell membranes of complex lipids from similar tissue.

The methods and apparatus of the present teaching provide analysis of clinical samples to rapidly aide surgical procedures. These methods and apparatus are particularly important based on the observation that if cancer cells remain after surgery, the tumor tissue may require further surgery, chemotherapy, or radiotherapy. Without some type of diagnostic aide, surgeons are often not able to determine during surgery whether every cancer cell and tissue has been removed, so healthy tissue may be removed for safety's sake alone. Therefore, using the methods and apparatus of the present teaching can reduce the amount of healthy tissue that is removed by monitoring tissue samples for cancerous cells during surgery. For example, current surgical practices may take at least 10-30 minutes for intervention related to tumor tissue or organ removal. It is important to remove the cancerous tissue while minimizing the damage to nearby healthy tissue. Also, antimicrobial therapy may be initiated through knowledge of the bacteriological results obtained during surgery. In general, the mass spectrometric analysis methods of the present teaching provide more information to the surgeon, shorten the time required for the surgery, reduce costs, and provide greater safety to the patient.

Thus, the MALDI-TOF mass spectrometer system of the present teaching provides numerous advantages over direct electrospray or rapid evaporative ionization mass spectrometry. One feature of the methods and apparatus of the present teaching is that, unlike the DESI and REIMS methods, the mass spectrometer module 204 is not directly connected to the patient or surgeon. Instead, the mass spectrometer module 204 can be located outside the immediate sterile surgical environment. The MALDI-TOF mass spectrometer processing module 204 is typically located in close proximity to the surgical environment. In some embodiments, the MALDI-TOF mass spectrometer is in the operating room. In other embodiments, the MALDI-TOF mass spectrometer is outside of the operating room. However, one skilled in the art will appreciate that the MALDI-TOF mass spectrometer processing module 204 only needs to be in a location where it can be rapidly accessed to receive the tissue biopsy and to perform the required MALDI mass spectrometer measurements in the required time period.

In particular, the mass spectrometer sample preparation and analysis time can be very short compared to the time required for the surgery and acquisition of samples. For example, the time required to prepare multiple samples and load them into the MALDI-TOF system of the present teaching can be less than 1 minute. In some embodiments, parallel digestion of multiple samples is performed using immobilized enzymes. The parallel digestion of multiple samples is performed on a similar, 1 minute, time scale. High-resolution (25 µm) imaging can be carried out at rate of 4 mm$^2$/min. Using the methods and apparatus of the present teaching, if it takes 10 minutes to do the surgery and to take samples, the mass spectrometer can analyze at least 100 separate samples in that time.

Furthermore, with the MALDI-TOF mass spectrometer system of the present teaching, protein profiles, lipid profiles, and metabolic profiles can all be obtained on each sample as desired by the surgeon.

EQUIVALENTS

While the Applicant's teaching is described in conjunction with various embodiments, it is not intended that the Applicant's teaching be limited to such embodiments. On the contrary, the Applicant's teaching encompass various alternatives, modifications, and equivalents, as will be appreciated by those of skill in the art, which may be made therein without departing from the spirit and scope of the teaching.

I claim:

1. An apparatus for monitoring a surgical procedure, the apparatus comprising:
   a) a matrix-assisted laser desorption ionization time-of-flight (MALDI-TOF) mass spectrometer comprising a load lock that receives a sample plate supporting tissue samples for analysis, an ionization chamber configured to ionize the tissue samples, and an ion detector configured to detect the ionized samples;
   b) a first video camera that produces an optical image of an operating field of the surgical procedure and being configured to record a location of a tissue sample;
   c) a sample extracting device configured to extract the tissue sample at the location within the optical image of the operating field;
   d) a sample preparation system configured to prepare MALID-TOF samples by depositing an extract of the extracted tissue sample on the sample plate together with a MALDI matrix;
   e) a sample plate loading mechanism comprising at least one of a microtiter format or an array format that loads the sample plate into the MALDI-TOF mass spectrometer;
   f) a second video camera that produces an optical image of the sample plate and being configured to record a location of the extracted tissue sample on the sample plate together with the MALDI matrix on the sample plate; and
   g) a computer that records the images from first and second video cameras, correlates the location of the tissue sample in the operating field with the location of the tissue sample on the sample plate, acquires mass spectra data from the MALDI-TOF mass spectrometer, compares the mass spectra data to known mass spectra data to determine mass spectra data from extracted tissue sample that indicates a particular type of tumor, and displays results of the correlation and the comparison in real-time to a surgeon during the surgical procedure.

2. The apparatus for monitoring a surgical procedure of claim 1 wherein the MALDI-TOF mass spectrometer comprises a linear mass spectrometer.

3. The apparatus for monitoring a surgical procedure of claim 1 wherein the MALDI-TOF mass spectrometer comprises a tandem mass spectrometer.

4. The apparatus for monitoring a surgical procedure of claim 1 wherein the MALDI-TOF mass spectrometer comprises a reflector mass spectrometer.

5. The apparatus for monitoring a surgical procedure of claim 1 wherein the sample plate and the ion detector in the MALDI-TOF mass spectrometer are biased at ground potential.

6. The apparatus for monitoring a surgical procedure of claim 1 wherein the sample preparation system comprises a robot.

7. The apparatus for monitoring a surgical procedure of claim 1 wherein the sample preparation system comprises a manual sample plate loading mechanism.

8. The apparatus for monitoring a surgical procedure of claim 1 wherein the sample plate loading mechanism comprises an autoloader.

9. The apparatus for monitoring a surgical procedure of claim 1 wherein the sample plate comprises a bar code.

10. The apparatus for monitoring a surgical procedure of claim 9 wherein the MALDI-TOF mass spectrometer further comprises a bar code reader and processor that reads the bar code on the sample plate and correlates the sample plate with associated instructions.

11. The apparatus for monitoring a surgical procedure of claim 1 wherein the computer is configured to transmit data about the tissue sample to the MALDI-TOF mass spectrometer.

12. The apparatus for monitoring a surgical procedure of claim 1 wherein the computer is programmed to change parameters in the MALDI-TOF mass spectrometer based on the acquired mass spectral data.

13. The apparatus for monitoring a surgical procedure of claim 1 wherein the computer is configured to receive data about the tissue sample.

14. The apparatus for monitoring a surgical procedure of claim 1 wherein the computer is programmed to passively transmit data to the MALDI-TOF mass spectrometer.

* * * * *